United States Patent

McGhee et al.

Patent Number: 5,189,205
Date of Patent: Feb. 23, 1993

[54] PROCESS FOR PREPARING ISOCYANATES

[75] Inventors: William D. McGhee, St. Louis; Thomas E. Waldman, Chesterfield, both of Mo.

[73] Assignee: Monsanto Compamy, St. Louis, Mo.

[21] Appl. No.: 852,455

[22] Filed: Mar. 16, 1992

[51] Int. Cl.$^5$ ............................................. C07C 263/04
[52] U.S. Cl. ................................... 560/345; 560/338; 562/123; 562/507; 562/550; 562/555
[58] Field of Search ................ 560/338, 345; 562/423, 562/507, 550, 555

[56] References Cited

U.S. PATENT DOCUMENTS

| | | | |
|---|---|---|---|
| 3,481,967 | 12/1969 | Ottmann et al. | 560/341 |
| 4,130,576 | 12/1978 | Hedaya et al. | 560/338 |
| 4,192,815 | 3/1980 | Sheludyakov et al. | 560/338 |
| 4,341,898 | 7/1982 | Milligan et al. | 560/24 |
| 4,567,294 | 1/1986 | Dressel et al. | 562/555 |

OTHER PUBLICATIONS

Belforte et al., *Chem. Ber.* 121, 1891–1897, (1988).
Y. Hori et al., *Chemistry Express*, 1 (4), 224–227, (1986).

*Primary Examiner*—José G. Dees
*Assistant Examiner*—Vera C. Clarke
*Attorney, Agent, or Firm*—Kenneth D. Goetz; Paul, L. Passley; James C. Bolding

[57] ABSTRACT

A process for preparing isocyanates comprising (a) contacting carbon dioxide and a primary amine in the presence of an aprotic organic solvent and an organic, nitrogenous base to produce the corresponding ammonium carbamate salt, and (b) reacting the ammonium carbamate salt with an electrophilic or oxophilic dehydrating agent to produce the corresponding isocyanate. A second embodiment comprises recovering the ammonium carbamate salt of step (a) prior to reacting the ammonium carbamate salt with an electrophilic or oxophilic dehydrating agent in the presence of an aprotic organic solvent and an organic, nitrogenous base.

28 Claims, No Drawings

PROCESS FOR PREPARING ISOCYANATES

BACKGROUND OF THE INVENTION

The invention relates to a process for preparing isocyanates. In one aspect, the invention relates to a new and useful process for preparing isocyanates from primary amines, carbon dioxide and an electrophilic or oxophilic dehydrating agent.

Isocyanates, especially diisocyanates, are important commodity chemicals for use in applications such as preparation of urethane foam, urethane elastomers, coatings, insecticides, herbicides, and the like.

Commercially, the phosgenation of primary amines is by far the most widely used method for producing isocyanates. The use of phosgene, however, has several disadvantages. The phosgenation route is long, energy intensive and requires handling highly corrosive materials, e.g. hydrogen chloride, chlorine, sulfuric acid and nitric acid, and highly toxic reagents and intermediates, e.g. phosgene and chlorine Furthermore, the phosgenation route requires use of process equipment which can withstand high temperatures and highly corrosive conditions resulting in increased capital costs.

One non-phosgene method for the preparation of isocyanates involves reaction of primary amines and $CO_2$ with a cobalt or manganese compound to produce metal carbamate complexes followed by reaction with an acyl halide in the presence of a solvent as is disclosed by A. Belforte et al., Incorporation and Deoxygenation of Carbon Dioxide: A Metal-assisted Facile Conversion of Carbon Dioxide and Primary Amines To Isocyanates, Chem. Ber., 121, 1891-1897 (1988). However, the process described therein requires long reaction times and gives unsatisfactory yield of isocyanate for a commercially viable process.

Another non-phosgene route to isocyanates is found in U.S. Pat. No. 4,192,815 (Sheludyakov et al.) which discloses preparation of isocyanates by reacting a primary amine with $CO_2$ and hexamethyldisilazane in the presence of an acidic catalyst, e.g. $H_2SO_4$, followed by decomposition of the resulting silyl esters of carbamic acid in the presence of a dehydration agent. However, the process described therein requires long reaction times and is not commercially practicable.

A non-phosgene process for preparing isocyanates which is economical, commercially viable, and can produce isocyanates with high yield under mild reaction conditions and short reaction times is highly desirable.

SUMMARY OF THE INVENTION

It is an object of the invention to provide a process for preparing isocyanates. It is a further object of the invention to provide an efficient and economic process for preparing isocyanates that is commercially viable It is a still further object of the invention to provide a process for preparing isocyanates which are not easily synthesized via phosgene routes.

According to the invention, a process for preparing isocyanates is provided which comprises the steps of (a) contacting carbon dioxide and a primary amine in the presence of an aprotic organic solvent and an organic, nitrogenous base under conditions of time and temperature sufficient to produce the corresponding ammonium carbamate salt, and (b) reacting the ammonium carbamate salt with an electrophilic or oxophilic dehydrating agent under reaction conditions of time and temperature sufficient to produce the corresponding isocyanate. In one embodiment, the ammonium carbamate salt of step (a) is recovered prior to reacting the ammonium carbamate salt with an electrophilic or oxophilic dehydrating agent in the presence of an aprotic organic solvent and an organic, nitrogenous base.

DETAILED DESCRIPTION OF THE INVENTION

A first embodiment of the invention relates to a process for preparing isocyanates comprising the steps of: (a) contacting $CO_2$ and a primary amine in the presence of an aprotic organic solvent and an organic, nitrogenous base under reaction conditions of time and temperature sufficient to produce the corresponding ammonium carbamate salt, and (b) reacting the ammonium carbamate salt with an electrophilic or oxophilic dehydrating agent under reaction conditions of time and temperature sufficient to produce the corresponding isocyanate.

A second embodiment of the invention relates to a process for preparing isocyanates comprising the steps of: (a) contacting $CO_2$ and a primary amine in the presence of an aprotic organic solvent and an organic, nitrogenous base under reaction conditions of time and temperature sufficient to produce the corresponding ammonium carbamate salt, (b) recovering the ammonium carbamate salt, and (c) reacting the ammonium carbamate salt with an electrophilic or oxophilic dehydrating agent in the presence of an aprotic organic solvent and an organic, nitrogenous base under reaction conditions of time and temperature sufficient to produce the corresponding isocyanate.

The isocyanates made according to this invention are readily recoverable and well suited for use in preparation of urethane foams, elastomers and coatings, insecticides, and herbicides.

The isocyanates produced by the process of the invention can be represented by the formula

wherein $R_2$ is selected from the group consisting of linear or branched alkyl, alkenyl, cycloalkyl, cycloalkenyl, aryl, aralkyl, aralkenyl, alkenaryl and alkaryl radicals having 1 to about 22 carbon atoms, a radical represented by the formula

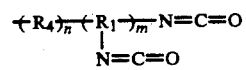

a radical represented by the formula

a radical represented by the formula

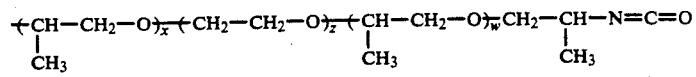

and a radical represented by the formula

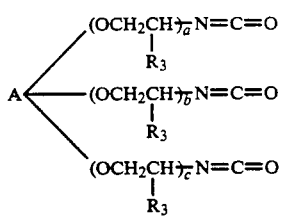

wherein $R_1$ and $R_4$ are independently selected from the group consisting of linear or branched alkyl, alkenyl, cycloalkyl, cycloalkenyl, aryl, aralkyl, aralkenyl, alkenaryl and alkaryl radicals having 1 to about 22 carbon atoms, m represents an integer from 0 to about 100, n represents an integer from 0 to about 8, $R_3$ is hydrogen or methyl, $x+w$ represents an integer from about 2 to about 70, z represents an integer from 0 to about 90, $x+w+z$ represents an integer from about 2 to about 100, a, b and c independently represent an integer from about 2 to about 30, and A represents a trihydric alcohol initiator such as glycerine or trimethylolpropane. In addition, $R_2$ may contain nonnucleophilic functional groups which do not react preferentially with the electrophilic or oxophilic dehydrating agent. Examples of suitable functional groups include esters, amides, urethanes, carbonates, and the like, and salts thereof.

Examples of isocyanates produced by the process of the invention include, but are not limited to, cyclohexyl isocyanate, octyl isocyanate, 1,4-cyclohexyl di-isocyanate, phenyl isocyanate, phenylalanine methyl ester isocyanate, glycine benzyl ester isocyanate, alanine benzyl ester isocyanate, phenylalanine ethyl ester isocyanate, leucine ethyl ester isocyanate, valine ethyl ester isocyanate, β-alanine ethyl ester isocyanate, glutamic acid diethyl ester isocyanate, hydrogenated toluene diisocyanate, hexamethylene diisocyanate, the diisocyanate of Jeffamine® D-400, and the like, and mixtures thereof.

The ammonium salt of the carbamate anion is prepared in solution in the presence of an organic, nitrogenous base. The reaction between the primary amine and carbon dioxide to form the ammonium carbamate salt may be represented by the equation (1). The resulting ammonium carbamate salt solutions are normally homogeneous.

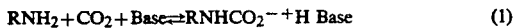

The result of the reaction of the ammonium carbamate salt with the electrophilic or oxophilic dehydrating agent may be represented by the equation (2).

The primary amines for use in the process of the invention are selected from the group consisting of compounds represented by the formula R—$NH_2$, polyoxyalkylene diamines represented by the formula and polyoxyalkylene triamines represented by the formula

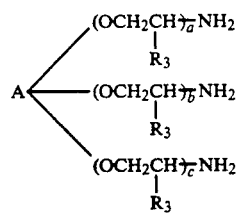

wherein R is selected from the group consisting of linear or branched alkyl, alkenyl, cycloalkyl, cycloalkenyl, aryl, aralkyl, aralkenyl, alkenaryl and alkaryl radicals having 1 to about 22 carbon atoms, a radical represented by the formula

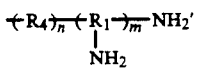

and a radical represented by the formula

—$R_4$—$NH_2$, wherein $R_1$, $R_3$, $R_4$, a, b, c, m, n, w, x, z and A are as defined above. Suitable primary amines include diamines and polyamines. In addition, R may contain nonnucleophilic functional groups which do not react preferentially with the electrophilic or oxophilic dehydrating agent. Examples of suitable functional groups include esters, amides, urethanes, carbonates, and the like, and salts thereof.

Examples of primary amines which can be employed in the process of the invention include cyclohexyl amine, octyl amine, 1,4-diaminocyclohexane, aniline, methyl amine, ethyl amine, n-propyl amine, isopropyl amine, n-butyl amine, isobutyl amine, t-butyl amine, n-pentyl amine, isopentyl amine, n-hexyl amine, n-octyl amine, benzyl amine, phenylalanine methyl ester hydrochloride salt, glycine benzyl ester p-toluene sulphonic acid salt, alanine benzyl ester hydrochloride salt, phenyl alanine ethyl ester hydrochloride salt, leucine ethyl ester hydrochloride salt, valine ethyl ester hydrochloride salt, β-alanine ethyl ester hydrochloride salt, 2,6-methylcyclohexyldiamine, 2,4-methylcyclohexyldiamine, n-hexyldiamine, 4,4'-methylene diphenyl amine, hexamethylene diamine, polyoxyalkylenediamines such as those available from Texaco Chemical Company under the trademark Jeffamine® including D-230 (approximate molecular weight=230), D-400 (approximate molecular weight=400), D-2000 (approximate molecular weight=2,000), D-4000 (approximate molecular weight=4,000), ED-600 (approximate molecular weight=600), ED-900 (approximate molecular weight=900), ED-2001 (approximate molecular weight=2,000), ED-4000 (approximate molecular weight=4,000) and ED-6000 (approximate molecular weight=6,000), polyoxyalkylene triamines such as those available from Texaco Chemical Company under the trademark Jeffamine® including T-403 (approxi-

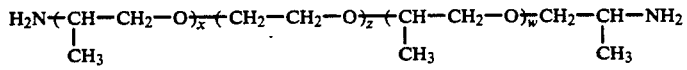

mate molecular weight=440), T-3000 (approximate molecular weight=3,000) and T-5000 (approximate molecular weight=5,000), tetraethylene pentamine, diethylene triamine, triethylene tetramine, pentaethylene hexamine, and the like, and mixtures thereof.

Applicable solvents for use in the process of the invention are aprotic organic solvents While both polar and non-polar aprotic organic solvents, as well as mixtures thereof, may be used, it is currently preferred to use non-polar aprotic organic solvents due to reduced occurrence of side reactions. As utilized herein, the phrase polar aprotic organic solvent means an aprotic organic solvent having a dielectric constant measured at 25° C. of greater than about 10ε as reported in Reichardt, C., Solvents and solvent effects in organic chemistry, 2nd ed., VCH Verlagsgesellschaft, Weinheim, (1988), Table A-1, utilizing toluene (2.38ε) and tetrahydrofuran (7.58ε) as standards measured at 25° C. Other methods for determining dielectric constants are known and suitable polar aprotic organic solvents are those having a dielectric constant greater than that of tetrahydrofuran utilizing any of such methods.

Examples of non-polar aprotic organic solvents which can be employed in the process of the invention include dichloromethane, toluene, tetrahydrofuran, o-dichlorobenzene, triethylamine and the like, and mixtures thereof. Currently preferred non-polar aprotic organic solvents include dichloromethane and toluene.

Examples of polar aprotic organic solvents which can be employed in the process of the invention include dimethyl formamide, N-methyl-2-pyrrolidone, N,N-dimethyl acetamide, dimethyl sulfoxide, acetonitrile, sulfolane, pyridine and the like, and mixtures thereof Currently preferred polar aprotic organic solvents include acetonitrile and N,N-dimethyl acetamide.

Although not specifically required, it is preferred to utilize the same solvent to carry out both reaction steps of the present invention in order to avoid additional process equipment for recovering additional solvents The amount of solvent utilized in the process of the invention is at least the amount necessary to solubilize the ammonium carbamate salt present.

To obtain high selectivities and yields for the desired isocyanates, an organic, nitrogenous base is employed in the process of the invention. The phrase "organic, nitrogenous base" as used herein refers to a base utilized in addition to the reactant primary amine. Applicable organic, nitrogenous bases for use in the process of the invention include guanidine compounds, amidine compounds, tertiary amines, pyridine and mixtures of any two or more thereof.

Examples of organic, nitrogenous bases which can be employed in the process of the invention include triethylamine, diethyl isopropylamine, trimethylamine, pyridine, tetramethyl guanidine (TMG), cyclohexyltetramethyl guanidine (CyTMG), butyltetraethyl guanidine (n-BTEG), cyclohexyl-tetraethyl guanidine (CyTEG), tetraethyl guanidine (TEG), t-butyl-tetraethyl guanidine (t-BTEG), 7-methyl-1,5,7-triazabicyclo[4.4.0]dec-5-ene, (MTBD), t-butyl-dimethyl formamidine (t-BDMF), t-butyldimethyl acetamidine (t-BDMA), 1,5-diazabicyclo[4.3.0]non-5-ene (DBN), 1,8-diazabicyclo[5.4.0]undec-7-ene (DBU) and the like, and mixtures of any two or more thereof.

The preferred organic, nitrogenous base will depend on the electrophilic or oxophilic dehydrating agent used. When the electrophilic or oxophilic dehydrating agent is a halogen-containing compound, the choice of base or mixture of bases is not critical to achieve high yields. When the electrophilic or oxophilic dehydrating agent is not a halogen-containing compound, the preferred base is a guanidine or amidine compound or if a mixture of bases is used, at least one base of the mixture of bases is preferably a guanidine or amidine compound.

The amount of organic, nitrogenous base utilized in the process of the invention will depend upon the particular embodiment of the process.

In the first embodiment wherein the ammonium carbamate salt is not recovered prior to reaction with the electrophilic or oxophilic dehydrating agent, the amount of organic, nitrogenous base can be conveniently expressed in terms of a ratio based on the number of equivalents of amine in the primary amine charged. Broadly, the ratio of the number of moles of organic, nitrogenous base to the number of equivalents of amine in the primary amine will be about 1:1 to about 20:1, preferably about 2:1 to about 10:1, and most preferably about 2:1 to about 4:1. The organic, nitrogenous base can be completely charged at the beginning of the process, or a portion may be charged at the beginning of the process and the remainder charged at any time prior to the reaction of the ammonium carbamate salt with the electrophilic or oxophilic dehydrating agent.

In the second embodiment wherein the ammonium carbamate salt is recovered prior to reaction with the electrophilic or oxophilic dehydrating agent, the amount of organic, nitrogenous base can be conveniently expressed in terms of a ratio based on the number of equivalents of amine in the primary amine charged for the reaction of the primary amine with carbon dioxide, and the amount of organic, nitrogenous base can be conveniently expressed in terms of a ratio based on the number of equivalents of carbamate in the ammonium carbamate salt charged for the reaction of the ammonium carbamate salt with the electrophilic or oxophilic dehydrating agent. For the reaction of the primary amine with carbon dioxide, the ratio of the number of moles of organic, nitrogenous base to the number of equivalents of amine in the primary amine will broadly be about 0.5:1 to about 10:1, preferably about 1:1 to about 5:1, and most preferably about 1:1 to about 2:1. For the reaction of the ammonium carbamate salt with the electrophilic or oxophilic dehydrating agent, the ratio of the number of moles of organic, nitrogenous base to the number of equivalents of carbamate in the ammonium carbamate salt will broadly be about 0.5:1 to about 10:1, preferably about 1:1 to about 5:1, and most preferably about 1:1 to about 2:1.

Applicable electrophilic or oxophilic dehydrating agents for use in the process of the invention include $POX_3$, $PX_3$, $SOX_2$, $SO_2X_2$, $SO_3$, $PX_5$, $P_2O_5$, $NO_y$, $NOX$, ketene, acid anhydrides having the formula

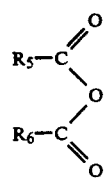

acid halides having the formula

and halides or oxyhalides of metals selected from the group consisting of transition metals, Group III B metals, Group IV B metals, and Group V B metals, and mixtures thereof wherein $R_5$ and $R_6$ are independently selected from the group consisting of fluoroalkyl, alkyl, aryl, alkaryl and aralkyl radicals having 1 to about 22 carbon atoms, X is chlorine or bromine, halides are chlorides or bromides, and y is 1 or 2. The periodic table nomenclature used herein is that of the International Union of Pure and Applied Chemistry (IUPAC).

Examples of suitable electrophilic or oxophilic dehydrating agents include $POCl_3$, $PCl_3$, $PBr_3$, $SOCl_2$, $PCl_5$, NO, $NO_2$, NOCl, $AlCl_3$, $VOCl_3$, $AlBr_3$, $TiBr_4$, $BBr_3$ and $TiCl_4$.

Examples of acid anhydrides which can be employed in the process of the invention include acetic anhydride, benzoic anhydride, propionoic anhydride, trifluoroacetic anhydride, and the like, and mixtures thereof. The currently preferred acid anhydride is acetic anhydride.

Examples of acid halides which can be employed in the process of the invention include acetyl chloride, acetyl bromide, benzoyl chloride, propionyl chloride, and the like, and mixtures thereof. The currently preferred acid halide is acetyl chloride.

The currently preferred electrophilic or oxophilic dehydrating agents are $POCl_3$, $PCl_3$ and $SOCl_2$ because of the extremely high yields achievable with these compounds under mild reaction conditions. However, when halide containing electrophilic or oxophilic dehydrating agents are used, halide salts are generated and must be handled as a waste byproduct. The formation of halide salt byproduct can be avoided if a non-halide containing electrophilic or oxophilic dehydrating agent, such as acetic anhydride or $SO_3$, is used.

In the first embodiment wherein the ammonium carbamate salt is not recovered prior to reaction with the electrophilic or oxophilic dehydrating agent, the amount of electrophilic or oxophilic dehydrating agent can be conveniently expressed in terms of a ratio based on the number of equivalents of amine in the primary amine charged. Broadly, the ratio of the number of moles of electrophilic or oxophilic dehydrating agent to the number of equivalents of amine in the primary amine will be about 0.4:1 to about 2:1, preferably about 0.9:1 to about 1:1:1 and most preferably 1:1.

In the second embodiment wherein the ammonium carbamate salt is recovered prior to reaction with the electrophilic or oxophilic dehydrating agent, the amount of electrophilic or oxophilic dehydrating agent can be conveniently expressed in terms of a ratio based on the number of equivalents of carbamate in the ammonium carbamate salt charged for the reaction of the ammonium carbamate salt with the electrophilic or oxophilic dehydrating agent. Broadly, the ratio of the number of moles of electrophilic or oxophilic dehydrating agent to the number of equivalents of carbamate in the ammonium carbamate salt will be about 0.4:1 to about 2:1, preferably about 0.9:1 to about 1.1:1, and most preferably about 1:1.

The reaction between the primary amine and carbon dioxide is conducted under a $CO_2$ atmosphere. The pressure of $CO_2$ during this reaction is 0 psig (atmospheric pressure) to about 150 psig, preferably 0 psig to about 100 psig, and most preferably 0 psig to about 80 psig. It is preferred to charge the $CO_2$ to the reaction vessel containing the primary amine below the liquid level in the reaction vessel. Although not specifically required, it is preferred to conduct the reaction of ammonium carbamate salt with electrophilic or oxophilic dehydrating agent under a $CO_2$ atmosphere. However, the reaction of ammonium carbamate salt with electrophilic or oxophilic dehydrating agent can be conducted under any inert atmosphere, e.g. nitrogen, argon or air, provided the atmosphere is substantially dry. A substantially dry atmosphere is critical because water will react with the electrophilic or oxophilic dehydrating agent. The pressure during this reaction is 0 psig to about 150 psig, preferably 0 psig to about 100 psig, and most preferably 0 psig to about 80 psig.

The temperature and time used in the process of the invention will depend on the particular reaction involved. For the reaction of primary amine with $CO_2$, the temperature is about $-78°$ C. to about 100° C., preferably about 10° C. to about 40° C., and most preferably about 20° C. to about 30° C. The time will broadly be the time required to achieve complete mixing of reactants to about 4 hours, preferably about 5 minutes to about 1 hour, and most preferably about 10 minutes to about 30 minutes. For the reaction of ammonium carbamate salt with electrophilic or oxophilic dehydrating agent, the temperature is about $-78°$ C. to about 100° C., preferably about $-20°$ C. to 30° C., and most preferably about $-10°$ C. to about 10° C. The time will broadly be the time required to achieve complete mixing of the reactants to about 4 hours, preferably about 1 minute to about 30 minutes, and most preferably about 5 minutes to about 10 minutes.

For the embodiment where the ammonium carbamate salt is recovered prior to reaction with the electrophilic or oxophilic dehydrating agent, the ammonium carbamate salt can be recovered by any conventional means known in the art.

The desired isocyanates produced by the process of the invention can be recovered by any conventional means known in the art, such as that disclosed in the examples herein.

Contemplated equivalence of the general formulas set forth above for the primary amines and isocyanates are compounds otherwise corresponding thereto and having the same general properties wherein one or more of the various R groups are simple variations of the substituents as defined therein.

In addition, where a substituent is designated as, or can be, a hydrogen, the exact chemical nature of a substituent which is other than hydrogen at that position is not critical so long as it does not adversely effect the overall synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

The invention will now be further disclosed in the following illustrative examples wherein parts and percentages are given on a molar basis unless otherwise specified.

EXAMPLES

All amines used in the following examples were obtained either from Aldrich Chemical Company or Kodak Chemical Company and were used as received. Amino acid ester hydrochlorides were obtained from either Sigma or Aldrich Chemical Company. Anhydrous solvents under nitrogen, DBU (1,8-diazabicyclo[5.4.0]undec-7-ene), $SO_2Cl_2$, acetyl chloride, acetic anhydride, $SO_3$-trimethylamine, and $PCl_3$ were purchased from Aldrich Chemical Company; MTBD (7-methyl-1,5,7triazabicyclo[4.4.0]dec-5-ene) was obtained from Flucka; thionyl chloride from Kodak; $POCl_3$ from Fisher Scientific; CyTMG(N-cyclohexyl-N',N',N'',N''-tetramethyl guanidine) and CyTEG(N-cyclohexyl-N',N',N'',N''-tetraethyl guanidine) were synthesized according to the general procedure set forth in Bredereck, H. and Bredereck, K., Chem Ber., 94, 2278–2295 (1961). Carbon dioxide was supplied either from Matheson (bone dry grade) or from Acetylene Gas Company (welding grade) and used without any further purification.

Gas chromatographic analysis was performed on a Varian model 3400 gas chromatograph with a model 8000 auto sampler using a 30 meter Megabore DB-I (3 μm) J & W Scientific column. Isocyanate products were purified and were identified by H NMR and IR spectroscopy. Nuclear Magnetic Resonance spectra were obtained on Varian VXR-300 or VXR-400 spectrometers. Infrared spectra were obtained on a Nicolet FT-IR.

The following examples, namely Examples 1–16, illustrate a variety of isocyanates prepared according to the teaching of the present invention. The results of Examples 1–16 are summarized in Table I.

EXAMPLE 1

Cyolohexyl isocyanate: Carbon dioxide was added subsurface to a dichloromethane ($CH_2Cl_2$) (30 mL) solution containing cyclohexylamine ($CyNH_2$) (0.04 mol, 3.96 g), N-cyclohexyl-N',N',N'',N''-tetraethylguanidine (CyTEG) (0.04 mol, 10.2 g) and triethylamine ($Et_3N$) (0.08 mol, 8.0 g) at −10° C. (ice and salt bath) for 1 h at a pressure of 0 psig. The reaction mixture was transferred via cannula all at once under carbon dioxide to the precooled solution of phosphorus oxychloride ($POCl_3$) (0.04 mol, 6.2 g) in 30 mL dichloromethane. After stirring for ca. 30 min at −10° C. the reaction mixture turned yellow-brown and a ppt. formed. The crude reaction was filtered and the filtrate concentrated in vacuo. The residue was extracted with 2×100 mL diethyl ether. The ether layers (light yellow) were concentrated and the residue was distilled under vacuum (ca. 0.1–0.3 torr) collecting product, cyclohexyl isocyanate, at 31°–33° C. (3.7 g, 74%) of 99% purity as judged by GC. IR (neat) 2255 cm$^{-1}$. $^1$H NMR (CDCl$_3$) δ 3.36–3.44 (m, 1H, 1.82–1.91 (m, 2H), 1.62–1.73 (m 2H) 1.38–1.50 (m 3H), 1.23–1.35 (m, 3H) uppm.

EXAMPLE 2

Cyclohexyl isocyanate: Carbon dioxide was added subsurface to a dichloromethane (20 mL) solution containing cyclohexylamine (0.02 mol, 1.98 g), triethylamine (0.06 mol, 6.0 g) at −10° C. (ice and salt bath) for 30 min at a pressure of 0 psig. The reaction mixture was transferred via cannula all at once under carbon dioxide to the precooled solution of phosphorus oxychloride (0.02 mol, 3.2 g) in 20 mL dichloromethane. After stirring ca. 30 min at −10° C. a white ppt formed. The ppt was filtered off and the filtrate concentrated in vacuo. The residue was extracted with 3×20 mL diethyl ether. The ether layers (light yellow) were 20 concentrated and the residue was distilled under vacuum collecting product, cyclohexyl isocyanate, at 31°–33° C. (1.45 g, 58%) of 97% purity as judged by GC. IR (neat) 2261 cm$^{-1}$. $^1$H NMR (CDCl$_3$) δ 3.44–3.39 (m, 1H), 1.90–1.85 (m, 2H), 1.72–1.68 (m, 2H), 1.50–1.41 (m, 2H), 1.33–1.20 (m, 3H) ppm.

EXAMPLE 3

Octyl isocyanate: Carbon dioxide was added subsurface to a dichloromethane (30 mL) solution containing octylamine (n-OctylNH$_2$) (0.04 mol, 5.2 g), N-cyclohexyl-N',N',N'',N''-tetraethylguanidine (0.04 mol, 10.2 g) and triethylamine (0.08 mol, 8.0 g) at −10° C. (ice and salt bath) for 1 h at a pressure of 0 psig. The reaction mixture was transferred via cannula all at once under carbon dioxide to the precooled solution of phosphorus oxychloride (0.04 mol, 6.2 g) in 30 mL dichloromethane. After stirring for ca. 30 min at −10° C. the reaction mixture turned yellow-brown and a ppt. formed. The crude reaction was filtered and the filtrate concentrated in vacuo. The residue was extracted with 2×100 mL diethyl ether. The ether layers (light yellow) were concentrated and the residue was distilled under vacuum (ca. 0.1–0.3 torr) collecting product, octyl isocyanate, at 42°–44° C. (3.9 g, 63%) of 99% purity as by GC. IR (neat) 2274 cm$^{-1}$. $^1$H NMR (in CDCl$_3$) δ 3.23–3.29 (t, 2H), 1.54–1.63 (m, 2H), 1.23–1.40 (br, 10H), 0.84–0.90 (t, 3H) ppm.

EXAMPLE 4

Octyl isocyanate: Carbon dioxide was added subsurface to a dichloromethane (20 mL) solution containing mol, 6.0 g) at −10° C. (ice and salt bath) for 30 min at a pressure of 0 psig. The reaction mixture was transferred rapidly via cannula under carbon dioxide to the precooled solution of phosphorus oxychloride (0.02 mol, 3.2 g) in 20 mL dichloromethane. After stirring for ca. 30 min at −10° C. a white ppt formed. The ppt was filtered off and the filtrate was concentrated in vacuo. The residue was extracted with 3×20 mL diethyl ether. The ether layer were concentrated and the residue was distilled under vacuum (ca. 0.1–0.3 torr) collecting product, octyl isocyanate, at 42°–44° C. (2.2 g, 71%) of 99% purity as judged by GC. IR (neat) 2274 cm$^{-1}$. $^1$H NMR (CDCl$_3$) δ 3.265 (t, 2H, J=6.6), 1.613-1.543 (m, 2H), 1.29 (br, 10H), 0.866 (t, 3H, J=6.6) ppm.

EXAMPLE 5

1,4-Cyclohexyl di-isocyanate: Carbon dioxide was added subsurface to a dichloromethane (50 mL) solution containing 1,4-diaminocyclohexane (1,4-(NH$_2$)$_2$C$_6$H$_{10}$) (mixture of cis and trans, 0.04 mol, 4.6 g), N-cyclohexyl-N',N',N'',N''-tetraethylguanidine (0.08 mol, 20.4 g) and triethylamine (0.08 mol, 8.0 g) at −10° C. (ice and salt bath) for 1 h at a pressure of 0 psig. The reaction mixture was transferred rapidly via cannula under carbon dioxide to the precooled solution of phosphorus oxychloride (0.08 mol, 12.4 g) in 50 mL dichloromethane. After stirring for ca. 30 min at −10° C. the reaction mixture turned yellow-brown and a ppt formed. The crude reaction was filtered and the filtrate concentrated in vacuo. The residue was extracted with 2×100 mL diethyl ether. The ether layers (light yellow) were concentrated and the residue was distilled under vacuum (ca. 0.1–0.3 torr) collecting product, cis and trans 1,4-cyclohexyl di-isocyanate, at 68°–78 ° C. (3.9 g, 57%) of 96% purity as judged by GC. IR (neat) 2266 cm$^{-1}$. $^1$H NMR was also obtained.

EXAMPLE 6

1,4-Cyclohexyl di-isocyanate: Carbon dioxide was added subsurface to a dichloromethane (30 mL) solution containing 1,4-diaminocyclohexane (mixture of cis and trans, 0.02 mol 2.30 g) and triethylamine (0.12 mol, 12.0 g) at −10° C. (ice and salt bath) for 40 min at a pressure of 0 psig. The reaction mixture was transferred rapidly via cannula under carbon dioxide to the precooled solution of phosphorus oxychloride (0.04 mol, 6.2 g) in 30 mL dichloromethane. After stirring for ca. 30 min at −10° C. a white ppt formed. The ppt. was filtered off and the filtrate concentrated in vacuo. The residue was extracted with 3×30 mL diethyl ether. The ether layers were concentrated and the residue was distilled under vacuum (ca. 0.1–0.3 torr) collecting product, 1,4-cyclohexyl di-isocyanate, at 68°–78° C. (2.0 g, 60%) of 99% purity as judged by GC. IR (neat) 2266 cm$^{-1}$. $^1$H NMR (CDCl$_3$) δ 3.61 (br, 2H), 2.03–2.01 (m, 1H), 1.86–1.70 (m, 6H), 1.54–1.50 (m, 1H) ppm.

EXAMPLE 7

Phenyl isocyanate: Carbon dioxide was added subsurface to a dichloromethane (20 mL) solution containing aniline (Ph—NH$_2$) (0.02 mol, 1.86 g) and triethylamine (0.06 mol, 6.0 g) at −10° C. (ice and salt bath) for 40 min at a pressure of 0 psig. The reaction mixture was transferred rapidly via cannula under carbon dioxide to the precooled solution of phosphorus oxychloride (0.02 mol, 3.2 g) in 20 mL dichloromethane. After stirring for ca. 30 min at −10° C. a white ppt. formed. The ppt. was filtered off and the filtrate concentrated in vacuo. The residue was extracted with 3×20 mL diethyl ether. The ether layers were concentrated and the residue was distilled under vacuum (ca. 0.1–0.3 torr) collecting product, phenyl isocyanate, at 71°–73° C. (1.45 g, 61%) of 99% purity as judged by GC. IR (neat) 2266 cm$^{-1}$. $^1$H NMR (CDCl$_3$) δ 7.30 (t, 2H, J=7.8), 7.17 (t, 1H, J=7.5), 7.07 (d, 2H, J=6.7) ppm.

EXAMPLE 8

Phenylalanine methyl ester isocyanate: Carbon dioxide was added subsurface to a dichloromethane (20 mL) solution containing phenylalanine methylester hydrochloride salt (0.005 mol, 1.07 g), N-cyclohexyl-N',N',N'',N''-tetraethylguanidine (0.005 mol, 1.3 g) and triethylamine (0.02 mol, 2.0 g) at −10° C. (ice and salt bath) for 30 min at a pressure of 0 psig. The reaction mixture was transferred rapidly via cannula under carbon dioxide to a pre-cooled solution of phosphorus oxychloride (0.005 mol, 0.8 g) in 20 mL dichloromethane. After stirring for 20 min at −10° C. diethylether (40 mL) was added to the reaction mixture. A white ppt. formed and was filtered off. The filtrate was concentrated in vacuo and the residue was extracted with 3×20 mL diethylether. The ether layers were concentrated and the residue distilled under vacuum (ca. 0.1–0.3 torr) collecting product, phenylalanine methyl ester isocyanate, at 91°–93° C. (0.426 g, 41.6%) of 93% purity as judged by GC. IR (neat) 2253, 1745 cm$^{-1}$. $^1$H NMR (CDCl$_3$) δ 7.35–7.17 (m, 5H), 4.26 (dd, 1H, J$_{gem}$=7.7, J$_{vic}$=4.7), 3.79 (s, 3H), 3.15 (dd, 2H, J$_{gem}$=13.8, J$_{vic}$=4.7), 3.01 (dd, 1H, J$_{gem}$=13.8, J$_{vic}$=7.8) ppm.

EXAMPLE 9

Glycine benzyl ester isocyanate: Carbon dioxide was added subsurface to a dichloromethane (20 mL) solution containing glycine benzyl ester p-toluenesulfonic acid salt (0.01 mol, 3.37 g) and triethylamine (0.04 mol, 4.0 g) at −10° C. (ice and salt bath) for 30 min at a pressure of 0 psig. The reaction mixture was transferred via cannula all at once under carbon dioxide to the precooled solution of phosphorus oxychloride (0.01 mol, 1.6 g) in 20 mL dichloromethane. After stirring for 20 min at −10° C. diethylether (40 mL) was added to the reaction mixture. A white ppt formed and was filtered off. The filtrate was concentrated in vacuo and the residue was extracted with 3×20 mL diethylether. The ether layers were concentrated and the residue was distilled under vacuum (ca. 0.1–0.3 torr) collecting product, glycine benzyl ester isocyanate, at 105°–106° C. (0.91 g, 47.5%) of 98% purity as judged by GC. IR (neat) 2253, 1747 cm$^{-1}$. $^1$H NMR (CDCl$_3$) δ 7.37 (s, 5H), 5.24 (s, 2H), 3.96 (s, 2H) ppm.

EXAMPLE 10

Alanine benzyl ester isocyanate: Carbon dioxide was added subsurface to a dichloromethane (20 mL) solution containing alanine benzyl ester hydrochloride salt (0.003 mol, 0.65 g) and triethylamine (0.013 mol, 1.3 g) at −10° C. (ice and salt bath) for 30 min at a pressure of psig. The reaction mixture was transferred via cannula all at once under carbon dioxide to the precooled solution of phosphorus oxychloride (0.003 mol, 0.5 g) in 20 mL dichloromethane. After stirring for 20 min at −10°. C. diethylether (40 mL) was added to the reaction mixture. A white ppt formed and was filtered off. The filtrate was concentrated in vacuo and the residue was extracted with 3×20 mL diethylether. The ether layers were concentrated and the residue was distilled under vacuum (ca. 0.1–0.3 torr) collecting product, alanine benzyl ester isocyanate, at 95°–96° C. (0.19 g, 30.9%) of 99% purity as judged by GC. IR (neat) 2241, 1744 cm$^{-1}$. $^1$H NMR (CDCl$_3$) δ 7.36 (s, 5H), 5.22 (s, 2H), 4.10 (q, 1H, J=14.3), 1.49 (d, 3H, J=7.1) ppm.

EXAMPLE 11

Phenylalanine ethyl ester isocyanate: Carbon dioxide was added subsurface to a dichloromethane (40 mL) solution containing phenylalanine ethyl ester hydrochloride salt (0.02 mol, 4.6 g), N-cyclohexyl-N',N',N'',N''-tetraethylguanidine (0.02 mol, 5.1 g) and triethylamine (0.06 mol, 6.0 g) at −10° C. (ice and salt bath) for 40 min at a pressure of 0 psig. The reaction mixture was transferred rapidly via cannula under carbon dioxide to the precooled solution of phosphorus oxychloride (0.02 mol, 3.1 g) in 40 mL dichloromethane. After stirring for 20 min at −10° C. diethylether (50 mL) was added to the reaction mixture. A white ppt formed and was filtered off. The filtrate was concentrated in vacuo and the residue was extracted with 3×25 mL diethylether. The ether layers were concentrated and the residue was distilled under vacuum (ca. 0.1–0.3 torr) collecting product, phenylalanine ethyl ester isocyanate, at 96°–106° C. (2.85 g, 64.5%) of 99% purity as judged by GC. IR (neat) 2261, 1742 cm$^{-1}$. $^1$H NMR (CDCl$_3$) δ 7.34–7.18 (m, 5H), 4.24 (q, 2H, J=14.1), 4.23 (d, 1H, J=7.8), 3.141 (dd, 1H, J$_{gem}$=13.7, J$_{vic}$=4.8), 3.02 (dd, 1H, J$_{gem}$=13.8, J$_{vic}$=7.7), 1.28 (t, 3H, J=7.1) ppm.

EXAMPLE 12

Leucine ethyl ester isocyanate: Carbon dioxide was added subsurface to a dichloromethane (40 mL) solution containing leucine ethyl ester hydrochloride salt (0.025 mol, 4.89 g), N-cyclohexyl-N',N',N'',N''-tetraethylguanidine (0.025 mol, 6.3 g) and triethylamine (0.10 mol, 10.0 g) at −10° C. (ice and salt bath) for 40 min at a pressure of 0 psig. The reaction mixture was transferred via cannula all at once under carbon dioxide to the precooled solution of phosphorus oxychloride (0.025 mol, 3.9 g) in 40 mL dichloromethane. After stirring for 20 min at −10° C. diethylether (50 mL) was added to the reaction mixture. A white ppt formed and was filtered off. The filtrate was concentrated in vacuo and the residue was extracted with 3×25 mL diethylether. The ether layers were concentrated and the residue was distilled under vacuum collecting product, leucine ethyl ester isocyanate, at 53°–58° C. (3.74 g, 81%) of 98.4% purity as judged by GC. IR (neat) 2261, 1742 cm$^{-1}$. $^1$H NMR (CDCl$_3$) δ 4.23 (q, 2H, J=14.2), 3.98 (dd, 1H, J$_{gem}$=8.8, J$_{vic}$=5.5), 1.84–1.77 (m, 1H), 1.65–1.59 (m, 2H), 1.29 (t, 3H, J=7.2), 0.92 (t, 6H, J=6.7) ppm.

EXAMPLE 13

Valine ethyl ester isocyanate: Carbon dioxide was added subsurface to a dichloromethane (40 mL) solution containing valine ethyl ester hydrochloride salt (0.025 mol, 4.54 g), N-cyclohexyl-N',N',N'',N''-tetraethylguanidine (0.023 mol, 5.8 g) and triethylamine (0.10 mol, 10.0 g) at −10° C. (ice and salt bath) for 40 min at a pressure of 0 psig. The reaction mixture was transferred rapidly via cannula under carbon dioxide to the precooled solution of phosphorus oxychloride (0.025 mol, 3.9 g) in 40 mL dichloromethane. After stirring for 20 min at −10° C. diethylether (50 mL) was added to the reaction mixture. A white ppt formed and was filtered off. The filtrate was concentrated in vacuo and the residue was extracted with 3×25 mL diethylether. The ether layers were concentrated and the residue was distilled under vacuum collecting product, valine ethyl ester isocyanate, at 37°–40° C. (2.917 g, 68%) of 99% purity as judged by GC. IR (neat) 2253, 1740 cm$^{-1}$. $^1$H NMR (CDCl$_3$) δ 4.28–4.20 (m, 2H), 3.88 (d, 1H, J=3.8), 2.24–2.18 (m, 1H), 1.29 (t, 3H, J=7.2), 1.00 (d, 3H, J=6.9), 0.89 (d, 3H, J=6.8) ppm.

EXAMPLE 14

β-Alanine ethyl ester isocyanate: Carbon dioxide was added subsurface to a dichloromethane (40 mL) solution containing β-alanine ethyl ester hydrochloride salt (0.03 mol, 4.6 g), N-cyclohexyl-N',N',N'',N''-tetraethylguanidine (0.03 mol, 7.6 g) and triethylamine (0.12 mol, 12.0 g) at −10° C. (ice and salt bath) for 40 min at a pressure of 0 psig. The reaction mixture was transferred rapidly via cannula under carbon dioxide to the precooled solution of phosphorus oxychloride (0.03 mol, 4.8 g) in 40 mL dichloromethane. After stirring for 20 min at −10° C. diethylether (50 mL) was added to the reaction mixture. A white ppt formed and was filtered off. The filtrate was concentrated in vacuo and the residue was extracted with 3×25 mL diethylether. The ether layers were concentrated and the residue was distilled under vacuum collecting product, β-alanine ethyl ester isocyanate, at 37°–39° C. (2.74 g, 64%) of 97.3% purity as judged by GC. IR (neat) 2272, 1732 cm$^{-1}$. $^1$H NMR (CDCl$_3$) δ 4.16 (q, 2H, J=4.3), 3.56 (t, 2H, J=6.4), 2.57 (t, 2H, J=6.4), 1.25 (t, 3H, J=7.2) ppm.

EXAMPLE 15

Glutamic acid diethyl ester isocyanate: Carbon dioxide was added subsurface to a dichloromethane (40 mL) solution containing glutamic acid ethyl ester hydrochloride salt (0.02 mol, 4.8 g) N-cyclohexyl-N',N',N'',N''-tetraethylguanidine (0.02 mol, 5.1 g) and triethylamine (0.06 mol, 6.0 g) at −10° C. (ice and salt bath) for 40 min at a pressure of 0 psig. The reaction mixture was transferred rapidly via cannula under carbon dioxide to the precooled solution of phosphorus oxychloride (0.02 mol, 3.2 g) in 40 mL dichloromethane.

After stirring for 20 min at −10° C. diethylether (50 mL) was added to the reaction mixture. A white ppt formed and was filtered off. The filtrate was concentrated in vacuo and the residue was extracted with 3×25 mL diethylether. The ether layers were concentrated and the residue was distilled under vacuum (ca. 0.1–0.3 torr) collecting product, glutamic acid ethyl ester isocyanate, at 97°–108° C. (3.23 g, 71%) of 99% purity as judged by GC. IR (neat) 2249, 1736 cm$^{-1}$. $^1$H NMR (CDCl$_3$) δ 4.25 (q, 2H, J=14.3), 4.12 (q, 2H, J=14.3), 4.10 (2d, 1H, J$_{gem}$=8.6, J$_{vic}$=4.4), 2.45–2.40 (m, 2H), 2.25–2.14 (m, 1H), 2.04–1.94 (m, 1H), 1.29 (t, 3H, J=7.1), 1.240 (t, 3H, J=7.1) ppm.

EXAMPLE 16

Hydrogenated Toluene Di-isocyanate: A 100 mL Fischer-Porter bottle was charged with a mixture of 2,4 and 2,6-methylcyclohexyldiamines (0.64 g, 5 mmol; 80:20 weight percent, respectively), N-cyclohexyl-N',N',N'',N''-tetraethyl guanidine (5.06 g, 20 mmol), biphenyl (154 mg, 1 mmol internal G.C. Standard) and 25 mL of CH$_2$Cl$_2$. The reaction vessel was pressurized to 80 psig with CO$_2$ and rapid stirring was initiated. A second Fischer-Porter bottle was charged with phosphorous oxychloride (0.93 g, 10 mmol) and 25 mL CH$_2$Cl$_2$ then pressurized to 80 psig with CO$_2$. The solutions were stirred for one hour at 21° C. and then cooled to 0° C. prior to adding the carbamate salt to the phosphorous oxychloride solution. A one mL aliquot was removed from the reaction mixture after five minutes at 0° C., diluted in 10 mL of diethyl ether in order to precipitate the phosphorous salts, and subsequent analysis of the ether extract by G.C. indicated >98% conversion of the mixture of methylcyclohexyldiamines to the corresponding di-isocyanates. The reaction mixture was allowed to warm to room temperature and stirred for one hour at the end of which time the pressure was released and the solvent was removed by evaporation. Distillation of the resulting oil under reduced pressure (80° C., 1 mm Hg) gave 0.64 g (71% isolated yield) of a mixture of 2,4 and 2,6-methylcyclohexyldiisocyanate as a colorless oil. The infrared spectrum of the mixture of di-isocyanates exhibited several strong bands between ca. 2350 and 2260 cm$^{-1}$ assigned to the NCO stretch of the isocyanate moieties. Analytical data for the mixture: $^1$H NMR (CDCl$_3$) δ 4.05 (t, 1H, J=2 Hz), 3.85 (t, 1H, J=1 Hz), 3.64 (tt, 1H, J=5 Hz, 1 Hz), 3.35 (tt, 1H, J=6 Hz, 2 Hz), 2.4–1.48 (multiplets, 14H), 1.08 (d, 3H, J=10 Hz), 1.02 (d, 3H, J=12 Hz) 1.00 (d, 3H, J=8 Hz), 0.97 (d, 3H, J=9 Hz). G.C./Mass Spectrum (Retention Time, 150° C. isothermal; E.I., 17eV, 180° C.); m/z (relative percent): 8.93 min.; 180 (3.7), 137 (86.9), 122 (100.0), 109 (12.6). 9.24 min.; 180 (7.2), 137 (100.0), 122 (42.1), 110 (39.5).

philic or oxophilic dehydrating agent (0.01 mole) in 30 mL of the same solvent used in the previous reaction. Aliquots were taken periodically and diluted with diethyl ether (either a heavy oil or a white precipitate formed upon addition of diethyl ether and was separated from the etherial solution prior to G.C. analysis) and analyzed via G.C.

The results of this study are given in Table II.

EXAMPLE 18

This example illustrates the preparation of isocya-

TABLE 1

Conversion of Amines to Isocyanates Using $CO_2$, Base, $POCl_3$ as the "Dehydrating Agent", and $CH_2Cl_2$ as the Solvent

| Example No. | RNH$_2$ | CO$_2$, psig (b) | Base (a) | Base (a) | Isolated Yield % RNCO |
|---|---|---|---|---|---|
| 1 | CyNH$_2$ | 0 | CyTEG | 2 Et$_3$N | 74 |
| 2 | CyNH$_2$ | 0 | Et$_3$N | 2 Et$_3$N | 58 |
| 3 | n-Octyl NH$_2$ | 0 | CyTEG | 2 Et$_3$N | 63 |
| 4 | n-Octyl NH$_2$ | 0 | Et$_3$N | 2 Et$_3$N | 71 |
| 5 | 1,4-(NH$_2$)$_2$C$_6$H$_{10}$ | 0 | 2 CyTEG | 2 Et$_3$N | 57 |
| 6 | 1,4-(NH$_2$)$_2$C$_6$H$_{10}$ | 0 | Et$_3$N | 5 Et$_3$N | 60 |
| 7 | Ph-NH$_2$ | 0 | Et$_3$N | 2 Et$_3$N | 61 |
| 8 | Phenylalanine methyl ester hydrochloride salt | 0 | CyTEG | 4 Et$_3$N | 41.6 |
| 9 | glycine benzyl ester p-toluene sulfonic acid salt | 0 | Et$_3$N | 3 Et$_3$N | 47.5 |
| 10 | alanine benzyl ester hydrochloride salt | 0 | Et$_3$N | 3.33 Et$_3$N | 30.9 |
| 11 | phenylalanine ethyl ester hydrochloride salt | 0 | CyTEG | 3 Et$_3$N | 64.5 |
| 12 | leucine ethyl ester hydrochloride salt | 0 | CyTEG | 4 Et$_3$N | 81 |
| 13 | valine ethyl ester hydrochloride salt | 0 | 0.92 CyTEG | 4 Et$_3$N | 68 |
| 14 | β-alanine ethyl ester hydrochloride salt | 0 | CyTEG | 4 Et$_3$N | 64 |
| 15 | glutamic acid ethyl ester hydrochloride salt | 0 | CyTEG | 3 Et$_3$N | 71 |
| 16 | 2,4- and 2,6-methylcyclohexyl diamine | 80 | CyTEG | 3 CyTEG | 71 |

(a) moles Base per mole RNH$_2$
(b) 0 psig is equivalent to conducting the reaction at atmospheric pressure.

EXAMPLE 17

This example illustrates the preparation of isocyanates utilizing phosphorous oxychloride as the "dehydrating agent" for a variety of amines, bases and solvents. General Procedure: Carbon dioxide was added subsurface to a solvent, i.e. dichloromethane (CH$_2$Cl$_2$), acetonitrile (CH$_3$CN), o-dichlorobenzene (o-Cl$_2$C$_6$H$_4$) and tetrahydrofuran (THF), solution containing 30 mL solvent, an amine (typically 0.01 moles), N-cyclohexyl-N',N',N'',N''-tetraethylguanidine (0.01 moles, See Tables II–V for other bases used), triethylamine (0.02 moles, see Tables II–V for other bases used) and biphenyl (0.001 mole, as internal G.C. standard) at −10° C. (ice and salt bath) for 1 h in a round bottomed flask (addition at 80 psig was performed in a Fischer-Porter bottle attached to a Parr Pressure head). The reaction mixture was transferred via cannula all at once under carbon dioxide to the pre-cooled solution of the electronates utilizing thionyl chloride as the "dehydrating agent" for a variety of amines, bases and solvents according to the general procedure given in Example 17.

The results of this study are given in Table III.

EXAMPLE 19

This example illustrates the preparation of isocyanates utilizing acetic anhydride as the "dehydrating agent" for a variety of amines, bases and solvents according to the general procedure given in Example 17.

The results of this study are given in Table IV.

EXAMPLE 20

This example illustrates the preparation of isocyanates utilizing dichloromethane as the solvent for a variety of amines, bases and "dehydrating agents" according to the general procedure given in Example 17.

The results of this study are given in Table V.

TABLE II

Conversion of amines to isocyanates using carbon dioxide, base and phosphorous oxychloride as a "dehydrating agent"

| RNH$_2$ | CO$_2$$^{(b)}$ | Base$^{(a)}$ | Base$^{(a)}$ | Solvent | GC Yield % RNCO |
|---|---|---|---|---|---|
| CyNH$_2$ | 0 psig | CyTEG | CyTEG | CH$_2$Cl$_2$ | 90 |

TABLE II-continued

Conversion of amines to isocyanates using carbon dioxide, base and phosphorous oxychloride as a "dehydrating agent"

| RNH$_2$ | CO$_2$[b] | Base[a] | Base[a] | Solvent | GC Yield % RNCO |
|---|---|---|---|---|---|
| CyNH$_2$ | " | " | 2 Et$_3$N | " | 96–100 |
| CyNH$_2$ | " | Et$_3$N | " | " | 98 |
| CyNH$_2$ | 80 psig | CyTEG | CyTEG | " | 99 |
| CyNH$_2$ | " | " | 2 Et$_3$N | " | 100 |
| n-Octyl NH$_2$ | 0 psig | " | CyTEG | " | 78.5 |
| n-Octyl NH$_2$ | " | " | 2 Et$_3$N | " | 97 |
| n-Octyl NH$_2$ | " | DBU | " | " | 87 |
| n-Octyl NH2 | " | CyTMG | " | " | 98 |
| n-Octyl NH$_2$ | " | MTBD | " | " | 95.5 |
| n-Octyl NH$_2$ | " | (i-Pr)$_2$NEt | " | " | 96 |
| n-Octyl NH$_2$ | " | Et$_3$N | " | " | 98 |
| n-Octyl NH$_2$ | " | " | " | THF | 87 |
| n-Octyl NH$_2$ | " | " | " | CH$_3$CN | 95 |
| n-Octyl NH$_2$ | 80 psig | CyTEG | CyTEG | CH$_2$Cl$_2$ | 94 |
| n-Octyl NH$_2$ | " | " | 2 Et$_3$N | " | 93 |
| n-Octyl NH$_2$ | " | " | CyTEG | Toluene | 99 |
| n-Octyl NH$_2$ | " | " | " | o-Cl$_2$C$_6$H$_4$ | 90 |
| Ph-NH$_2$ | 0 psig | Et$_3$N | 2 Et$_3$N | CH$_2$Cl$_2$ | 94 |
| 1,4-(NH$_2$)$_2$C$_6$H$_{10}$ | 0 psig | CyTEG | " | " | 79 |
| 1,4-(NH$_2$)$_2$C$_6$H$_{10}$ | 0 psig | Et$_3$N | 2 Et$_3$N | " | 91 |
| 1,4-(NH$_2$)$_2$C$_6$H$_{10}$ | 80 psig | CyTEG | CyTEG | " | 77 |
| H$_2$N(CH$_2$)$_6$NH$_2$ | " | " | " | " | 67 |

All reactions run at −10° C.–0° C. using biphenyl as internal G.C. standard.
[a]moles Base per mole RNH$_2$
[b]0 psig is equivalent to conducting the reaction at atmospheric pressure.

TABLE III

Conversion of amines to isocyanates using carbon dioxide, base and thionyl chloride as "dehydrating agent"

| RNH$_2$ | CO$_2$[b] | Base[a] | Base[a] | Solvent | G.C. Yield % RNCO | % RNSO | % Urea |
|---|---|---|---|---|---|---|---|
| n-Octyl NH$_2$ | 0 psig | Et$_3$N | 2 Et$_3$N | CH$_2$Cl$_2$ | 48 | 3 | 18 |
| n-Octyl NH$_2$ | " | Et$_3$N | 2 ET$_3$N | Toluene | 60 | 23 | 8 |
| n-Octyl NH$_2$ | " | " | " | THF | 99 | 3 | — |
| n-Octyl NH$_2$ | " | " | " | CH$_3$CN | 76 | 7 | 8 |
| n-Octyl NH$_2$ | 80 psig | CyTEG | CyTEG | CH$_2$Cl$_2$ | 98 | 2 | — |
| n-Octyl NH$_2$ | " | MTBD | 2 pyr | " | 95 | 6 | — |
| n-Octyl NH$_2$ | " | DBU | DBU | " | 76.5 | 16 | — |
| n-Octyl NH$_2$ | " | " | 2 pyr | " | 71 | 28 | — |
| n-Octyl NH$_2$ | " | CyTEG | CyTEG | Toluene | 98 | — | — |
| n-Octyl NH$_2$ | " | " | 2 pyr | " | 100 | — | — |
| CyNH$_2$ | " | " | CyTEG | CH$_2$Cl$_2$ | 94 | 6.5 | — |
| CyNH$_2$ | " | " | 2 pyr | " | 76 | 16 | — |

All reactions run at −10° C.–0° C. using biphenyl as internal G.C. standard. % Yields of RNSO and Urea are approximate.
[a]moles Base per mole RNH$_2$
[b]0 psig is equivalent to conducting the reaction at atmospheric pressure.

TABLE IV

Conversion of amines to Isocyanates using carbon dioxide, base and acetic anhydride as a "dehydrating agent."

| RNH$_2$ | CO$_2$[b] | Base[a] | Base[a] | Solvent | GC Yield % RNCO |
|---|---|---|---|---|---|
| CyNH$_2$ | 0 psig | CyTEG | 2 Et$_3$N | CH$_2$Cl$_2$ | 54 |
| CyNH$_2$ | " | MTBD | " | " | 58 |
| CyNH$_2$ | " | DBU | " | " | 17 |
| CyNH$_2$ | " | (i-Pr)$_2$NEt | " | " | 1.5 |
| CyNH$_2$ | " | Et$_3$N | " | " | <1 |
| CyNH$_2$ | " | CyTEG | " | THF | 41 |
| CyNH$_2$ | " | " | " | Toluene | 44 |
| CyNH$_2$ | " | " | " | CH$_3$CN | 53 |
| CyNH$_2$ | 80 psig | CyTEG | " | CH$_2$Cl$_2$ | 66–70 |
| n-Octyl-NH$_2$ | 0 psig | " | 2 Et$_3$N | " | 11–24 |
| n-Octyl-NH$_2$ | 80 psig | " | " | " | 5 |
| 1,4-(NH$_2$)$_2$C$_6$H$_{10}$ | 80 psig | " | " | " | 59 |

All reactions run at −10° C.–0° C. using biphenyl as internal G.C. standard. All reactions run to completion with the acetamide as the major side product and in some cases a trace amount of di-alkylurea was detected.
[a]moles Base per mole RNH$_2$
[b]0 psig is equivalent to conducting the reaction at atmospheric pressure.

TABLE V

Conversion of amines to isocyanates using carbon dioxide, dichloromethane as the solvent, base and various "dehydrating agents."

| RNH$_2$ | CO$_2$[b] | Dehydrating Agent | Base[a] | Base[a] | G.C. Yield % RNCO |
|---|---|---|---|---|---|
| CyNH$_2$ | 0 psig | acetyl-Cl | CyTEG | 2 Et$_3$N | 42 |
| CyNH$_2$ | 80 psig | " | " | " | 30 |
| n-Octyl NH$_2$ | 0 psig | " | " | " | 25 |
| n-Octyl NH$_2$ | 80 psig | " | " | " | 14 |
| CyNH$_2$ | 0 psig | SO$_2$Cl$_2$ | CyTEG | 2 Et$_3$N | 38 |
| CyNH$_2$ | 80 psig | " | " | " | 42 |
| n-Octyl NH$_2$ | 0 psig | " | " | " | 61 |
| n-Octyl NH$_2$ | 80 psig | " | " | " | 43 |
| CyNH$_2$ | " | PCl$_3$ | CyTEG | 2 Et$_3$N | 97 |
| CyNH$_2$ | " | " | Et$_3$N | " | 92 |
| n-Octyl NH$_2$ | " | " | CyTEG | " | 99 |
| n-Octyl NH$_2$ | " | " | Et$_3$N | " | 93 |
| CyNH$_2$ | " | SO$_3$NMe$_3$ | CyTEG | CyTEG | 48 |
| CyNH$_2$ | 0 psig | " | " | " | 27 |
| CyNH$_2$ | " | " | " | 2 Et$_3$N | 7 |

TABLE V-continued

Conversion of amines to isocyanates using carbon dioxide, dichloromethane as the solvent, base and various "dehydrating agents."

| RNH$_2$ | CO$_2$[b] | Dehydrating Agent | Base[a] | Base[a] | G.C. Yield % RNCO |
|---|---|---|---|---|---|
| CyNH$_2$ | " | " | Et$_3$N | " | trace |

All reactions run at −10° C.–0° C. using biphenyl as internal G.C. standard.
[a]moles Base per mole RNH$_2$
[b]0 psig is equivalent to conducting the reaction at atmospheric pressure.

EXAMPLE 21

This example illustrates the preparation of cyclohexyl isocyanate.

Into a Fischer-Porter bottle was added 0.99 g (10 mmol) cyclohexyl amine, 4 g (20 mmol) cyclohexyltetramethyl guanidine, 154 mg biphenyl (1 mmol as internal standard for G.C. analysis), 20 mL N,N-dimethylacetamide (DMAC) and a stir bar. This was attached to a pressure head and ca. 100 psig carbon dioxide added above the solution. Upon addition of the carbon dioxide the solution warmed slightly. The solution was then cooled to 0° C. using an ice bath.

Into a second Fischer-Porter bottle was added 1.53 g (15 mmol) acetic anhydride in 20 mL N,N-dimethylacetamide and this was attached to a pressure head and 100 psig carbon dioxide added above the solution. This solution was cooled to 0° C. using an ice bath. After 1 h the carbamate solution from the first Fischer-Porter bottle was added to the solution of acetic anhydride under 100 psig CO$_2$ pressure at 0° C.. Upon addition the reaction mixture warmed to 7° C. After 1 h an aliquot was taken and analyzed by G.C. and I.R.

A yield of 90% was calculated for cyclohexyl isocyanate, I.R. in DMAC, 2263 cm$^{-1}$ (compared by G.C. and I.R. with authentic cyclohexyl isocyanate, 2263 cm$^{-1}$ in DMAC). The only other product observed was N-cyclohexylacetamide (6% by G.C.).

EXAMPLE 22

This example demonstrates the preparation and isolation of Hexamethylenediisocyanate (HMDI). A 100 mL Fischer-Porter bottle was charged with hexamethylenediamine substantially free of water (0.58 g, 5 mmol), cyclohexyltetraethyl guanidine (5.06 g, 20 mmol), and 25 mL of CH$_2$Cl$_2$. The reaction vessel was pressurized to 80 psig with CO$_2$ and rapid stirring was initiated. A second Fischer-Porter bottle was charged with phosphoryl chloride (0.93 g, 10 mmol) and 25 mL CH$_2$Cl$_2$, then pressurized to 80 psi with CO$_2$. The solutions were stirred for one hour at 21° C. and then cooled to 0° C. prior to adding the carbamate salt to the phosphoryl chloride solution. The reaction mixture was allowed to warm to room temperature and stirred for one hour at the end of which time the pressure was released and the solvent was removed on a rotovap. The desired diisocyanate was extracted from the resulting viscous oil with 2×100 mL portions of diethyl ether. The ether was removed on a rotovap to give a clear liquid which was distilled under reduced pressure (110° C., 20 mm Hg) yielding 0.76 g (90% isolated yield) of a hexamethylenediisocyanate as a colorless oil. The infrared spectrum of the diisocyanate exhibits a strong band at 2281 cm$^{-1}$ assigned to the NCO stretch of the socyanate.

EXAMPLE 23

This example demonstrates the preparation and isolation of Jeffamine® D-400 diisocyanate. A 100 mL Fischer-Porter bottle was charged with Jeffamine D-400 (2.0 g, ca. 5 mmol), cyclohexyltetraethyl guanidine (5.06 g, 20 mmol), and 25 mL of CH$_2$Cl$_2$. The reaction vessel was pressurized to 80 psig with CO$_2$ and rapid stirring was initiated. A second Fischer-Porter bottle was charged with phosphoryl chloride (0.93 g, 10 mmol) and 25 mL CH$_2$Cl$_2$, then pressurized to 80 psi with CO$_2$. The solutions were stirred for one hour at 21° C. and then cooled to 0° C. prior to adding the carbamate salt to the phosphoryl chloride solution. The reaction mixture was allowed to warm to room temperature and stirred for one hour at the end of which time the pressure was released and the solvent was removed on a rotovap. The desired diisocyanate was extracted from the resulting viscous oil with 2×100 mL portions of diethyl ether. The ether was removed on a rotovap to give a clear liquid which was distilled under dynamic vacuum (ca. 120° C., 0.5 mm Hg) yielding 1.08 g (48% isolated yield) of a Jeffamine D-400 diisocyanate as a pale yellow oil. The infrared spectrum of the diisocyanate exhibits a strong band at 2248 cm$^{-1}$ assigned to the NCO stretch of the isocyanate.

EXAMPLE 24

This example demonstrates the preparation and isolation of 2-methyl-1,5-pentanediisocyanate. A 200 mL Fischer-Porter bottle was charged with 2-methyl-1,5-pentanediamine (5.0 mL, 37 mmol), cyclohexyltetraethyl guanidine (18.7 g, 54 mmol), and 65 mL of CH$_2$Cl$_2$. The reaction vessel was pressurized to 80 psig with CO$_2$ and rapid stirring was initiated. A second Fischer-Porter bottle was charged with phosphoryl chloride (7.0 g, 55 mmol) and 50 mL CH$_2$Cl$_2$ then pressurized to 80 psi with CO$_2$. The solutions were stirred for 20 min. at 21° C. and then cooled to 0° C. prior to adding the carbamate salt to the phosphoryl chloride solution. The reaction mixture was allowed to warm to room temperature and stirred for one hour at he end of which time the pressure was released and the solvent was removed on a rotovap. The desired diisocyanate was extracted from the resulting viscous oil with 2×200 mL portions of diethyl ether. The ether extracts were filtered to remove the amine salts and the ether was removed on a rotovap to give a pale yellow liquid which was distilled under reduced pressure (108° C., 0.1 mm Hg) yielding 4.35 g (69% isolated yield) of a 2-methyl-1,5-pentanediisocyanate as a colorless oil. The infrared spectrum of the diisocyanate exhibits a strong band at 2286 cm$^{-1}$ assigned to the NCO stretch of the isocyanate. Analytical Data for 2-methyl-1,5-pentanediisocyanate: $^1$H NMR (CDCl$_3$): 3.36 (6, 2h, j=6.6 Hz), 3.26 (d of 4, 2H, J=6.0, 3.1 Hz), 1.80–1.41 (m, 4H), 1.30 (m, 1H), 1.02 (d, 3H, J=3.6 Hz). Infrared spectrum (neat): 2286.3 cm$^{-1}$ (NCO) B.P. 108° C. @ 0.1 mm Hg.

EXAMPLE 25

This example demonstrates the preparation of Cyclohexylisocyanate using trifluoroacetic anhydride as the "dehydrating agent." A 100 mL Fischer-Porter bottle was charged with cyclohexylamine (0.49 g, 5.0 mmol), cyclohexyltetraethyl guanidine (1.26 g, 5.0 mmol), biphenyl (0.15 g, 1 mmol; internal standard) and 25 mL of CH$_2$Cl$_2$. The reaction vessel was pressurized to 80 psig with CO$_2$ and rapid stirring was initiated. A second Fischer-Porter bottle was charged with trifluoroacetic anhydride (0.71 mL, 5.0 mmol) and 25 mL $CH_2Cl_2$ then pressurized to 80 psi with $CO_2$. The solutions were stirred for 20 min. at 21° C. and then cooled to 0° C. prior to adding the carbamate salt to the trifluoroacetic anhydride solution. A sample was taken after five minutes and diluted with diethyl ether and analyzed by gas chromatography. The yield of cyclohexylisocyanate was 90% relative to the biphenyl internal standard. The reaction mixture was allowed to warm to room temperature and stirred for one hour at the end of which time a second sample was taken giving an identical yield (90%) of cyclohexylisocyanate as determined by gas chromatography.

EXAMPLE 26

This example demonstrates the preparation of n-octylisocyanate using titanium tetrabromide as the "dehydrating agent." A 100 mL Fischer-Porter bottle was charged with n-octylamine (0.64 g, 5.0 mmol), cyclohexyltetraethyl guanidine (2.53 g, 10.0 mmol), biphenyl (0.15 g, 1 mmol; internal standard) and 25 mL of $CH_2Cl_2$. The reaction vessel was pressurized to 80 psig with $CO_2$ and rapid stirring was initiated. A second Fischer-Porter bottle was charged with titanium tetrabromide (1.84 g, 5.0 mmol) and 25 mL $CH_2Cl_2$, then pressurized to 80 psi with $CO_2$. The solutions were stirred for 20 minutes at 21° C. and then cooled to 0° C. prior to adding the carbamate salt to the suspension of titanium tetrabromide in $CH_2Cl_2$. A sample was taken after five minutes and diluted with diethyl ether and analyzed by gas chromatography. The yield of noctylisocyanate was 32% relative to the biphenyl internal standard. The reaction mixture was allowed to warm to room temperature and stirred for three hours at the end of which time a second sample was taken giving an identical yield (32%) of n-octylisocyanate as determined by gas chromatography.

EXAMPLE 27

This example demonstrates the preparation of cyclohexylisocyanate using aluminum trichloride as the "dehydrating agent." A 100 mL Fischer-Porter bottle was charged with cyclohexylamine (0.49 g, 5.0 mmol), triethylamine (2.78 mL, 20.0 mmol), biphenyl (0.15 g, 1 mmol; internal standard) and 25 mL of $CH_2Cl_2$. The reaction vessel was pressurized to 80 psig with $CO_2$ and rapid stirring was initiated. A second Fischer-Porter bottle was charged with aluminum trichloride (0.66 g, 5.0 mmol) and 25 mL $CH_2Cl_2$, then pressurized to 80 psi with $CO_2$. The solutions were stirred for 20 min. at 21° C. after which time the carbamate salt was added to the suspension of $AlCl_3$. A sample was taken after five 1 minutes and diluted with diethyl ether and analyzed by gas chromatography. The yield of cyclohexylisocyanate was 6.2% relative to the biphenyl internal standard. The reaction mixture was allowed to warm to room temperature and stirred for 28 hours at the end of which time a second sample was taken giving 9.0% yield of cyclohexylisocyanate as determined by gas chromatography.

EXAMPLE 28

This example demonstrates the preparation of n-octylisocyanate using vanadium oxytrichloride as the "dehydrating agent." A 100 mL Fischer-Porter bottle was charged with n-octylamine (0.64 g, 5.0 mmol), cyclohexyltetraethyl guanidine (2.53 g, 10.0 mmol), biphenyl (0.15 g, 1 mmol; internal standard) and 25 mL of $CH_2Cl_2$. The reaction vessel was pressurized to 80 psig with $CO_2$ and rapid stirring was initiated. A second Fischer-Porter bottle was charged with vanadium oxytrichloride (0.87 g, 5.0 mmol) and 25 mL $CH_2Cl_2$, then pressurized to 80 psi with $CO_2$. The solutions were stirred for 20 min. at 21° C. and then cooled to 0° C. prior to adding the carbamate salt to the solution of $OVCl_3$ in $CH_2Cl_2$. A sample was taken after five minutes and diluted with diethyl ether and analyzed by gas chromatography. The yield of n-octylisocyanate was 5% relative to the biphenyl internal standard. The reaction mixture was allowed to warm to room temperature and stirred for two hours at the end of which time a second sample was taken giving a yield of 8% n-octylisocyanate as determined by gas chromatography.

EXAMPLE 29

This example demonstrates the preparation of n-octylisocyanate using boron tribromide as the "dehydrating agent." A 100 mL Fischer-Porter bottle was charged with octylamine (0.64 g, 5.0 mmol), cyclohexyltetraethyl guanidine (2.53 g, 10.0 mmol), biphenyl (0.15 g, 1 mmol; internal standard) and 25 mL of $CH_2Cl_2$. The reaction vessel was pressurized to 80 psig with $CO_2$ and rapid stirring was initiated. A second Fischer-Porter bottle was charged with boron tribromide (1.26 g, 5.0 mmol) and 25 mL $CH_2Cl_2$, then pressurized to 80 psi with $CO_2$. The solutions were stirred for 20 minutes at 21° C. after which time the carbamate salt was added to the solution of $BBr_3$. A sample was taken after five minutes and diluted with diethyl ether and analyzed by gas chromatography. The yield of cyclohexylisocyanate was 13% relative to the biphenyl internal standard. The reaction mixture was stirred for 24 hours at the end of which time a second sample was taken giving 26% yield of cyclohexylisocyante and 30% di-n-octyl urea (85% conversion of amine) as determined by gas chromatography.

That which is claimed is:
1. A process for preparing an isocyanate comprising:
   (a) contacting $CO_2$ and a primary amine in the presence of an aprotic organic solvent and an organic, nitrogenous base, under reaction conditions of time and temperature sufficient to produce the corresponding ammonium carbamate salt, and
   (b) reacting said ammonium carbamate salt with an electrophilic or oxophilic dehydrating agent selected from the group consisting of $POX_3$, $PX_3$, $SOX_2$, $SO_2X_2$, $SO_3$, $PX_5$, $P_2O_5$, $NO_y$, $NOX$, ketene, acid anhydrides having the formula

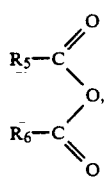

acid halides having the formula

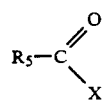

and halides or oxyhalides of metals selected from the group consisting of transition metals, Group III B metals, Group IV B metals, and Group V B metals, wherein $R_5$ and $R_6$ are independently selected from the group consisting of alkyl, fluoroalkyl, aryl, alkaryl and aralkyl radicals having 1 to about 22 carbon atoms and X is chlorine or bromine, halides are chlorides or bromides, and y is 1 or 2 under reaction conditions of time and temperature sufficient to produce the corresponding isocyanate.

2. The process according to claim 1 wherein said aprotic organic solvent is selected from the group consisting of dichloromethane, tetrahydrofuran, acetonitrile, o-dichloromethane, toluene, N,N-dimethylacetamide and pyridine.

3. The process according to claim 2 wherein said aprotic organic solvent is present in at least an amount sufficient to solubilize said ammonium carbamate salt.

4. The process according to claim 1 wherein said organic, nitrogenous base is selected from the group consisting of guanidine compounds, amindine compounds, tertiary amines, pyridine and mixtures thereof.

5. The process according to claim 4 wherein said organic, nitrogenous base is a mixture of at least two bases selected from the group consisting of guanidine compounds, amidine compounds, tertiary amines and pyridine.

6. The process according to claim 5 wherein at least one base of said mixture is selected from the group consisting of guanidine compounds and amidine compounds.

7. The process according to claim 4 wherein the ratio of the number of moles of said organic, nitrogenous base to the number of equivalents of amine in said primary amine starting material is 1:1 to about 20:1.

8. The process according to claim 7 wherein the ratio of the number of moles of said organic, nitrogenous base to the number of equivalents of amine in said primary amine starting material is about 2:1 to about 10.1.

9. The process according to claim 1 wherein said electrophilic or oxophilic dehydrating agent is selected from the group consisting of $POCl_3$, $SOCl_2$, $SO_2Cl_2$, acetic anhydride, acetyl chloride, $SO_3$, $PCl_3$, trifluoroacetic anhydride, $TiBr_4$, $AlCl_3$, $VOCl_3$ and $BBr_3$.

10. The process according to claim 1 wherein the ratio of the number of moles of said electrophilic or oxophilic dehydrating agent to the number of equivalents of amine in said primary amine starting material is about 0.4:1 to about 2:1.

11. The process according to claim 1 wherein said primary amine is selected from the group consisting of compounds represented by the formula R—$NH_2$, polyoxyalkylene diamines represented by the formula

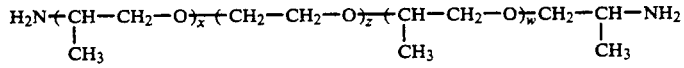

and polyoxyalkylene trimamines represented by the formula

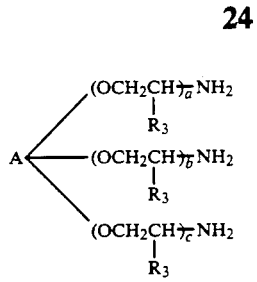

wherein R is selected from the group consisting of linear or branched alkyl, alkenyl, cycloalkyl, cycloalkenyl, aryl, aralkyl, aralkenyl, alkenaryl and alkaryl radicals having 1 to about 22 carbon atoms, a radical represented by the formula

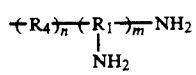

and a radical represented by the formula —$R_4$—$NH_2$, or R as defined above containing nonnucleophilic functional groups; wherein $R_1$ and $R_4$ are independently selected from the group consisting of linear or branched alkyl, alkenyl, cycloalkyl, cycloalkenyl, aryl, aralkyl, aralkenyl, alkenaryl and alkaryl radicals having 1 to about 22 carbon atoms, m represents an integer from 0 to about 100, n represents an integer from 0 to about 8, $R_3$ is hydrogen or methyl, x+w represents an integer from about 2 to about 70, z represents an integer from 0 to about 90, x+w+z represents an integer from about 2 to about 100, a, b and c independently represent an integer from about 2 to about 30, and A represents a trihydric alcohol initiator.

12. The process according to claim 11 wherein said nonnucleophilic functional groups are selected from the group consisting of esters, amides, urethanes, carbonates and salts thereof.

13. A process according to claim 1 wherein said isocyanate is represented by the formula $$R_2-N=C=O$$

wherein $R_2$ is selected from the group consisting of linear or branched alkyl, alkenyl, cycloalkyl, cycloalkenyl, aryl, aralkyl, aralkyl, alkenaryl and alkaryl radicals having 1 to about 22 carbon atoms, a radical represented by the formula

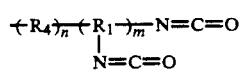

a radical represented by the formula $$-R_4-N=C=O,$$

and a radical represented by the formula

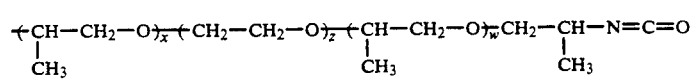

or $R_2$ as defined above containing nonnucleophilic functional groups;
or said isocyanate is represented by the formula

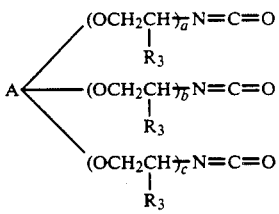

wherein $R_1$ and $R_4$ are independently selected from the group consisting of linear or branched alkyl, alkenyl, cycloalkyl, cycloalkenyl, aryl, aralkyl, aralkenyl, alkenaryl and alkaryl radicals having 1 to about 22 carbon atoms, m represents an integer from 0 to about 100, n represents an integer from 0 to about 8, $R_3$ is hydrogen or methyl, $x+w$ represents an integer from about 2 to about 70, z represents an integer from 0 to about 90, $x+w+z$ represents an integer from about 2 to about 100, a, b and c independently represent an integer from about 2 to about 30, and A represents a trihydric alcohol initiator.

14. The process according to claim 13 wherein said nonnucleophilic functional groups are selected from the group consisting of esters, amides, urethanes, carbonates and salts thereof.

15. A process for preparing an isocyanate comprising:
(a) contacting $CO_2$ and a primary amine in the presence of an aprotic organic solvent and an organic, nitrogenous base, under reaction conditions of time and temperature sufficient to produce the corresponding ammonium carbamate salt,
(b) recovering said ammonium carbamate salt,
(c) reacting said ammonium carbamate salt with an electrophilic or oxophilic dehydrating agent selected from the group consisting of $POX_3$, $PX_3$, $SOX_2$, $SO_2X_2$, $SO_3$, $PX_5$, $P_2O_5$, $NO_y$, NOX, ketene, acid anhydrides having the formula

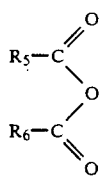

acid halides having the formula

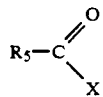

and halides or oxyhalides of metals selected from the group consisting of transition metals, Group III B metals, Group IV B metals, and Group V B metals, wherein $R_5$ and $R_6$ are independently selected from the group consisting of alkyl, fluoroalkyl, aryl, alkaryl and aralkyl radicals having 1 to about 22 carbon atoms and X is chlorine or bromine, halides are chlorides or bromides, and y is 1 or 2 in the presence of an aprotic organic solvent and an organic, nitrogenous base under reaction conditions of time and temperature sufficient to produce the corresponding isocyanate.

16. The process according to claim 15 wherein said aprotic organic solvent is selected from the group consisting of dichloromethane, tetrahydrofuran, acetonitrile, o-dichlorobenzene, toluene, N,N-dimethylacetamide and pyridine.

17. The process according to claim 16 wherein said aprotic organic solvent is present in at least an amount sufficient to solubilize said ammonium carbamate salt.

18. The process according to claim 15 wherein said organic, nitrogenous base is selected from the group consisting of guanidine compounds, amidine compounds, tertiary amines, pyridine and mixtures thereof.

19. The process according to claim 18 wherein said organic, nitrogenous base is a mixture of at least two bases selected from the group consisting of guanidine compounds, amidine compounds, tertiary amines and pyridine.

20. The process according to claim 19 wherein at least one base of said mixture is selected from the group consisting of guanidine compounds and amidine compounds.

21. The process according to claim 18 wherein the ratio of the number of moles of said organic, nitrogenous base to the number of equivalents of amine in said primary amine starting material in step (a) is 0.5:1 to about 10:1, and the ratio of the number of moles of said organic, nitrogenous base to the number of equivalents of carbamate in said ammonium carbamate salt starting material in step (c) is 0.5:1 to about 10:1.

22. The process according to claim 21 wherein the ratio of the number of moles of said organic, nitrogenous base to the number of equivalents of amine in said primary amine starting material in step (a) is 1:1 to about 5:1, and the ratio of the number of moles of said organic, nitrogenous base to the number of equivalents of carbamate in said ammonium carbamate salt starting material in step (c) is 1:1 to about 5:1.

23. The process according to claim 5 wherein said electrophilic or oxophilic dehydrating agent is selected from the group consisting of $POCl_3$, $SOCl_2$, $SO_2Cl_2$, acetic anhyride, acetyl chloride, $SO_3$, $PCl_3$, trifluoroacetic anhydride, $TiBr_4$, $AlCl_3$, $VOCl_3$ and $BBr_3$.

24. The process according to claim 15 wherein the ratio of the number of moles of said electrophilic or oxophilic dehydrating agent to the number of equivalents of carbamate in said ammonium carbamate salt starting material in step (c) is about 0.4:1 to about 2:1.

25. The process according to claim 15 wherein said primary amine is selected from the group consisting of compounds represented by the formula R—$NH_2$, polyoxyalkylene diamines represented by the formula

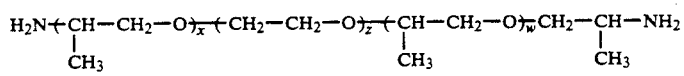

and polyoxyalkylene triamines represented by the formula

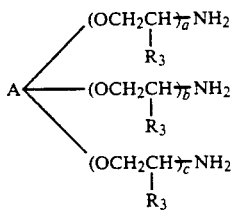

wherein R is selected from the group consisting of linear or branched alkyl, alkenyl, cycloalkyl, cycloalkenyl, aryl, aralkyl, aralkyl, alkenaryl and alkaryl radicals having 1 to about 22 carbon atoms, a radical represented by the formula

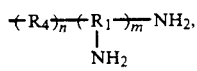

and a radical represented by the formula —$R_4$—$NH_2$, or R as defined above containing nonnucleophilic functional groups; wherein $R_1$ and $R_4$ are independently selected from the group consisting of linear or branched alkyl, alkenyl, cycloalkyl, cycloalkenyl, aryl, aralkyl, aralkenyl, alkenaryl and alkaryl radicals having 1 to about 22 carbon atoms, m represents an integer from 0 to about 100, n represents an integer from 0 to about 8, $R_3$ is hydrogen or methyl, $x+w$ represents an integer from about 2 to about 70, z represents an integer from 0 to about 90, $x+w+z$ represents an integer from about 2 to about 100, a, b and c independently represent an integer from about 2 to about 30, and A represents a trihydric alcohol initiator.

26. The process according to claim 25 wherein said nonnucleophilic functional groups are selected from the group consisting of esters, amides, urethanes, carbonates and salts thereof.

27. A process according to claim 15 wherein said isocyanate is represented by the formula $$R_2-N=C=O$$

wherein $R_2$ is selected from the group consisting of linear or branched alkyl, alkenyl, cycloalkyl, cycloalkenyl, aryl, aralkyl, aralkyl, alkenaryl and alkaryl radicals having 1 to about 22 carbon atoms, a radical represented by the formula

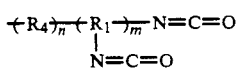

a radical represented by the formula $$-R_4-N=C=O,$$

and a radical represented by the formula

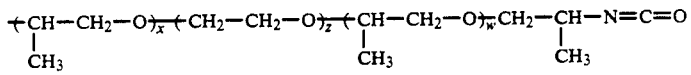

or $R_2$ as defined above containing nonnucleophilic functional groups;
or said isocyanate is represented by the formula

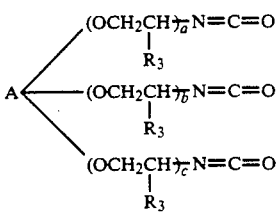

wherein $R_1$ and $R_4$ are independently selected from the group consisting of linear or branched alkyl, alkenyl, cycloalkyl, cycloalkenyl, aryl, aralkyl, aralkenyl, alkenaryl and alkaryl radicals having 1 to about 22 carbon atoms, m represents an integer from 0 to about 100, n represents an integer from 0 to about 8, $R_3$ is hydrogen or methyl, $x+w$ represents an integer from about 2 to about 70, z represents an integer from 0 to about 90, $x+w+z$ represents an integer from about 2 to about 100, a, b and c independently represent an integer from about 2 to about 30, and A represents a trihydric alcohol initiator.

28. The process according to claim 27 wherein said nonnucleophilic functional groups are selected from the group consisting of esters, amides, urethanes, carbonates and salts thereof.

* * * * *